(12) United States Patent
Snyder et al.

(10) Patent No.: US 12,426,940 B2
(45) Date of Patent: Sep. 30, 2025

(54) ELECTRODE ASSEMBLIES WITH NON-CONTACT TEMPERATURE SENSING FOR THERMAL MEASUREMENTS

(71) Applicant: Solta Medical Ireland Limited, Dublin (IE)

(72) Inventors: Kevin John Snyder, Redmond, WA (US); Frederick Jay Bennett, Bellevue, WA (US); Rolf T. Boone, Kirkland, WA (US); Craig Collins, Woodinville, WA (US)

(73) Assignee: Solta Medical Ireland Limited, Dublin (IE)

( * ) Notice: Subject to any disclaimer, the term of this patent is extended or adjusted under 35 U.S.C. 154(b) by 550 days.

(21) Appl. No.: 17/908,935

(22) PCT Filed: Mar. 4, 2021

(86) PCT No.: PCT/EP2021/055472
§ 371 (c)(1),
(2) Date: Sep. 2, 2022

(87) PCT Pub. No.: WO2021/175996
PCT Pub. Date: Sep. 10, 2021

(65) Prior Publication Data
US 2023/0089551 A1    Mar. 23, 2023

Related U.S. Application Data

(60) Provisional application No. 62/985,458, filed on Mar. 5, 2020.

(51) Int. Cl.
*A61B 18/14*    (2006.01)
*A61B 18/00*    (2006.01)

(52) U.S. Cl.
CPC .... *A61B 18/14* (2013.01); *A61B 2018/00791* (2013.01); *A61B 2018/147* (2013.01)

(58) Field of Classification Search
CPC .......... A61B 18/14; A61B 2018/00791; A61B 2018/147; A61B 5/01; A61B 5/4836;
(Continued)

(56) References Cited

U.S. PATENT DOCUMENTS 5,522,662 A * 6/1996 Shiokawa ............... G01J 5/046
374/E13.003
7,473,251 B2 * 1/2009 Knowlton .............. A61B 90/02
606/41

(Continued)

FOREIGN PATENT DOCUMENTS

CN    102348425 A    2/2012
CN    110639128 A1   1/2020
(Continued)

OTHER PUBLICATIONS

Taiwan Intellectual Property Office; Examination Report issued in Taiwanese Patent Application No. 110107300 on Nov. 6, 2024; 23 pages.

(Continued)

*Primary Examiner* — Michael F Peffley
(74) *Attorney, Agent, or Firm* — Thompson Hine LLP

(57) ABSTRACT

Devices for directing electromagnetic energy to tissue during cosmetic procedures, as well as methods of treatment and methods of device manufacture. An electrode assembly includes a housing, an electrode, and a thermal sensor arranged inside the housing. The electrode, which includes an aperture, is configured to deliver electrical energy to a targeted area of a patient. The thermal sensor is positioned relative to the aperture of the electrode to provide a field of view through the aperture to a surface of the targeted area.

(Continued)

The thermal sensor is configured to generate sensor data indicative of a temperature at the surface of the targeted area, and to thereby provide non-contact temperature sensing.

20 Claims, 6 Drawing Sheets

(58) Field of Classification Search
CPC .......... A61B 5/4848; A61N 2005/0644; A61N 1/40; G01J 5/0025
See application file for complete search history.

(56) References Cited

U.S. PATENT DOCUMENTS

| 9,161,802 | B2* | 10/2015 | Przybyszewski | A61B 18/14 |
| 11,273,316 | B2* | 3/2022 | Collins | A61B 18/1815 |
| 2004/0111087 | A1 | 6/2004 | Stern et al. | |
| 2007/0198004 | A1 | 8/2007 | Altshuler et al. | |
| 2008/0200861 | A1* | 8/2008 | Shalev | A61Q 9/04 |
| | | | | 604/20 |
| 2008/0200969 | A1* | 8/2008 | Weber | A61N 1/06 |
| | | | | 374/E13.002 |
| 2009/0149930 | A1 | 6/2009 | Schenck | |
| 2010/0179531 | A1 | 7/2010 | Nebrigic et al. | |
| 2011/0015687 | A1* | 1/2011 | Nebrigic | A61B 18/18 |
| | | | | 607/2 |
| 2013/0278226 | A1 | 10/2013 | Cong et al. | |
| 2014/0188099 | A1 | 7/2014 | Przybyszewski | |
| 2014/0266235 | A1 | 9/2014 | Mathur | |
| 2017/0007146 | A1 | 1/2017 | Schulhauser et al. | |

FOREIGN PATENT DOCUMENTS

| TW | M434931 U | 8/2012 |
| WO | 2007106339 A2 | 9/2007 |
| WO | 2016070134 A1 | 5/2016 |

OTHER PUBLICATIONS

European Patent Office, International Search Report and Written Opinion issued in International Patent Application No. PCT/EP2021/055472, 11 pages (Jun. 6, 2021).

Taiwan Intellectual Property Office; Examination Report issued in Taiwanese Patent Application No. 110107300 on May 10, 2024; 19 pages.

Taiwan Intellectual Property Office; Examination Report issued in Taiwanese Patent Application No. 110107300 on Jul. 31, 2024; 22 pages.

* cited by examiner

ELECTRODE ASSEMBLIES WITH NON-CONTACT TEMPERATURE SENSING FOR THERMAL MEASUREMENTS

TECHNICAL FIELD

The invention described herein relates generally to devices for directing electromagnetic energy to tissue during cosmetic procedures, and in particular, to temperature sensing for such devices.

Devices deliver electrical energy towards a targeted area of a patient for various cosmetic procedures, such as skin tightening, skin contouring, or hair removal. When such devices direct electromagnetic energy towards a targeted area of tissue during a cosmetic procedure, accurate measurement of temperatures at the targeted area is important to ensure effective cosmetic effect and avoid patient discomfort. Such devices generally include one or more thermistors positioned proximate to a non-patient facing side of an electrode delivering electromagnetic energy to obtain temperature measurements at the targeted area. However, temperature measurements obtained from those thermistors may be of limited use during a cosmetic procedure for various reasons.

For example, such sensor data is generally unable to accurately measure the actual surface temperature of the targeted area of tissue. Instead, sensor data generated by a thermistor quantifies temperature at the location of the thermistor. Intervening between the thermistor and the targeted area proximate to a patient-facing side of the electrode is a printed circuit upon which the electrode is generally formed, and any other elements formed on that printed circuit.

Other environmental factors occurring during a cosmetic procedure may further impact an ability of a thermistor to accurately measure temperature at a surface of the targeted area. By way of example, during a cosmetic procedure, electromagnetic radiation associated with delivery of electromagnetic energy to the targeted area may impart electromagnetic interference on sensor data generated by the thermistor. As another example, the thermistor may be sprayed with a portion of coolant that a coolant source delivers to the non-patient facing side of the electrode during a cosmetic procedure.

Thus, it may be desirable to provide such energy-based devices with improved temperature sensing.

SUMMARY

Embodiments of the invention described herein include electrode assemblies for use in a device configured to deliver electromagnetic energy as part of a cosmetic procedure and methods of performing cosmetic procedures using such electrode assemblies. In an embodiment, an electrode assembly includes a housing, an electrode, and a thermal sensor arranged inside the housing. The electrode includes an aperture, and the electrode is configured to direct electrical energy to a targeted area of a patient. The thermal sensor is configured to generate sensor data indicative of temperature at a surface of the targeted area measured via the aperture.

In an embodiment, an apparatus includes an electrode assembly comprising an electrode with an aperture. The electrode is configured to direct electrical energy to a targeted area of a patient. The apparatus further includes a handpiece configured to removably receive the electrode assembly. The apparatus further includes a first circuit and a second circuit that are each arranged inside the handpiece. The first circuit is configured to electrically couple the electrode with a generator. The second circuit is configured to electrically couple a temperature sensor arranged inside a housing of the electrode assembly with a controller. The temperature sensor is configured to generate sensor data indicative of temperature at a surface measured by the thermal sensor via the aperture.

In an embodiment, a system includes an electrode assembly, a generator coupled to the electrode assembly, and a controller coupled with the generator and the electrode assembly. The electrode assembly includes a housing, an electrode, and a thermal sensor arranged inside the housing. The electrode is configured to deliver electrical energy to a targeted area of a patient. The thermal sensor is configured to generate sensor data indicative of temperature at a surface of the targeted area measured via an aperture of the electrode. The generator is configured to generate the electrical energy. The controller is configured to regulate the electrical energy generated by the generator based on the sensor data.

In an embodiment, a method includes heating a targeted area of patient tissue with electrical energy delivered from an electrode, and sensing a temperature of a surface of the targeted area with a non-contact temperature sensor to generate temperature data. The electrode and the non-contact temperature sensor may be located inside a housing, and the electrode may include an aperture through which the non-contact temperature sensor has a field of view to the surface of the targeted area.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention. In the drawings, like reference numerals are used to indicate like parts in the various views.

DETAILED DESCRIPTION

Figure 1:
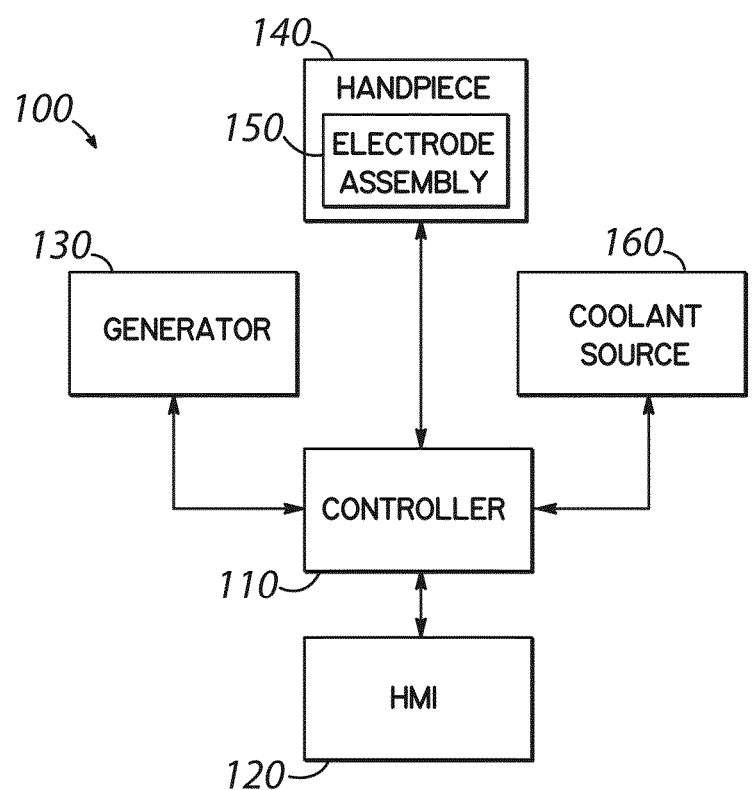
FIG. 1 is a block diagram of an example energy-based device that is suitable for implementing aspects of the invention described herein.

FIG. 1 is a block diagram of an example energy-based device 100 that is suitable for implementing aspects of the invention described herein. In operation, device 100 is configured to deliver energy towards a targeted area of a patient, as part of a cosmetic procedure (e.g., skin tightening, tattoo removal, hair removal, and the like). By way of example, device 100 may be configured to deliver electrical energy within a high frequency range of the electromagnetic spectrum to a targeted area of a patient. The delivered electrical energy may heat tissue within the targeted area to produce a cosmetic effect, such as altering collagen within a dermis layer to modify a consistency and/or geometry of an epidermis layer overlaying the dermis layer.

While device 100 is described as delivering electrical energy (e.g., radiofrequency ("RF") energy) as part of a cosmetic procedure in the embodiment of FIG. 1, one skilled in the art will recognize that device 100 may also deliver other forms of energy for cosmetic purposes. For example, device 100 may deliver radiant energy (e.g., laser and/or intense pulsed light energy), acoustic energy (e.g., ultrasound), thermal energy, mechanical energy, and the like.

As depicted in FIG. 1, device 100 includes controller 110, human-to-machine interface ("HMI") 120, generator 130, handpiece 140, a tip in the form of electrode assembly 150, and coolant source 160. Controller 110 is generally configured to control the operation and functionality of device 100 by controlling the other components of device 100, such as generator 130 and coolant source 160. In controlling the other components of device 100, controller 110 enables the application or delivery of energy to a targeted area of a patient.

HMI 120 provides an interface between an operator and device 100 for exchanging commands, requests, information, data, and the like, which enable the operator to interact with the functionalities provided by device 100. In an embodiment, HMI 120 includes a touch-sensitive touch screen that provides both an input interface and an output interface between the operator and device 100. In an embodiment, HMI 120 may include an audio interface, such as a microphone. In an embodiment, HMI 120 may include physical input devices, such as buttons (e.g., push buttons, rocker buttons, etc.), dials, slider switches, joysticks, click wheels, a keyboard, a pointer device (e.g., a mouse), and the like. In an embodiment, HMI 120 includes a physical input device disposed on an outward facing surface of handpiece 140.

Generator 130 is configured to generate electrical energy for driving elements of the electrode assembly 150 when enabled by controller 110 and in accordance with commands received from an operator via HMI 120. To that end, generator 130 comprises circuitry that is operative convert electrical power from an external power source (e.g., an alternating current ("AC") outlet) into electrical energy with parameters (e.g., a center frequency, amplitude, duty cycle, and the like) specified by controller 110. Examples of such circuitry includes: a tuner, a reference oscillator, an impedance matching network, an amplifier, and the like.

Handpiece 140 is configured to couple electrode assembly 150 to the other components of device 100 along an energy propagation path. Handpiece 140 is mechanically coupled to device 100 via a flexible conduit comprising cabling that electrically couples handpiece 140 to the other components of device 100 and tubing that defines a fluid path for coolant output by coolant source 160. During a cosmetic procedure, an operator positions handpiece 140 (and thereby electrode assembly 150) proximate to a targeted area of a patient. The operator instructs device 100 to deliver energy for a limited duration to the targeted area by interacting with one or more input devices (e.g., a button and/or a switch) disposed on an outward surface of handpiece 140. For example, handpiece 140 may include one or more input devices that enable the operator to initiate/terminate energy delivery to the targeted area and adjust an amount of energy that is applied to the targeted area.

Electrode assembly 150 may be detachably coupled with handpiece 140. In an embodiment, the generator 130 may generate radiofrequency ("RF") energy, and electrode assembly 150 may deliver RF energy generated by generator 130 to a patient to perform a cosmetic procedure. Electrode assembly 150 includes electrode patterns that are designed to deliver the electrical energy in a specific pattern and density to the patient during the cosmetic procedure. In an embodiment, electrode assembly 150 is configured to be driven by generator 130 in a monopolar configuration. When electrode assembly 150 is driven in a monopolar configuration, device 100 further includes a return pad. The return pad provides a return path for current from the targeted area of the patient to device 100 during the cosmetic procedure. In an embodiment, electrode assembly 150 is configured to be driven by generator 130 in a bipolar configuration. When electrode assembly 150 is driven in a bipolar configuration, device 100 would not include a return pad. Instead, electrode assembly 150 includes at least one additional electrode that provides a return path RF current from the targeted area of the patient to device 100 during the cosmetic procedure.

Coolant source 160 is configured to deliver coolant to an interior surface of electrode assembly 150 to control a temperature of an electrode of electrode assembly 150 during cosmetic procedures. That coolant is delivered to the electrode of electrode assembly 150 via a fluid path arranged inside handpiece 140 and a lumen of electrode assembly 150 fluidly coupling coolant source 160 with the electrode.

In accordance with various embodiments, sensor data indicative of temperatures associated with operation of device 100 is obtained using one or more thermal sensors (e.g., a non-contact thermal sensor) included in electrode assembly 150. As discussed in greater detail below, such sensor data may include sensor data that measures the temperature of skin located within a targeted area while device 100 delivers electrical energy to the targeted area. During a cosmetic procedure, such sensor data is communicated to controller 110 for use in regulating the operation of generator 130 and/or coolant source 160.

Figure 2:
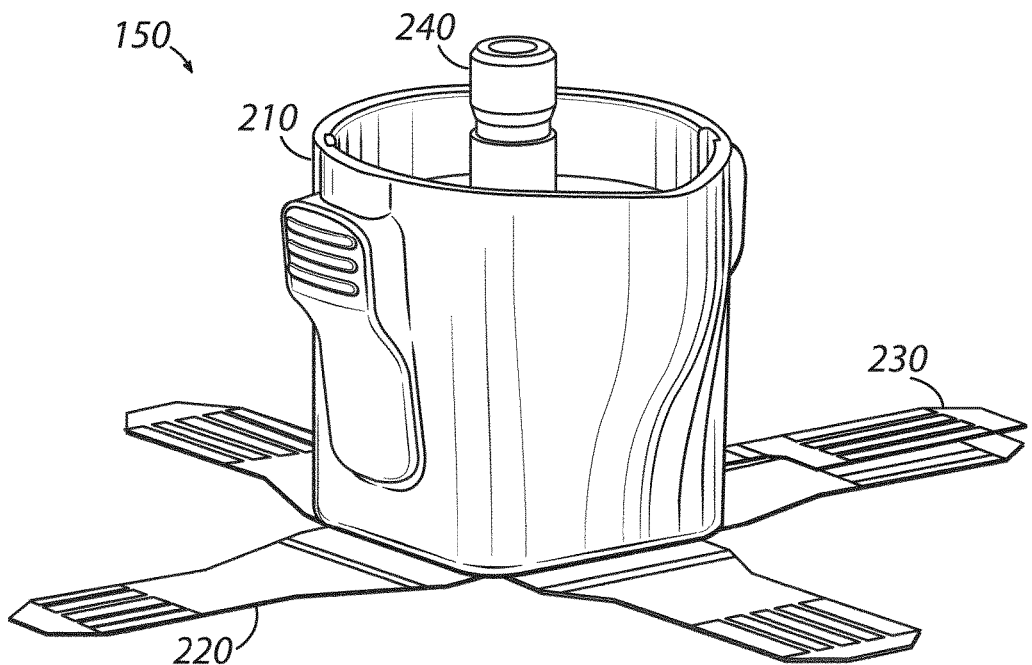
FIG. 2 is a perspective view of an example electrode assembly for an energy-based device that is suitable for implementing aspects of the invention described herein.
Figure 3:
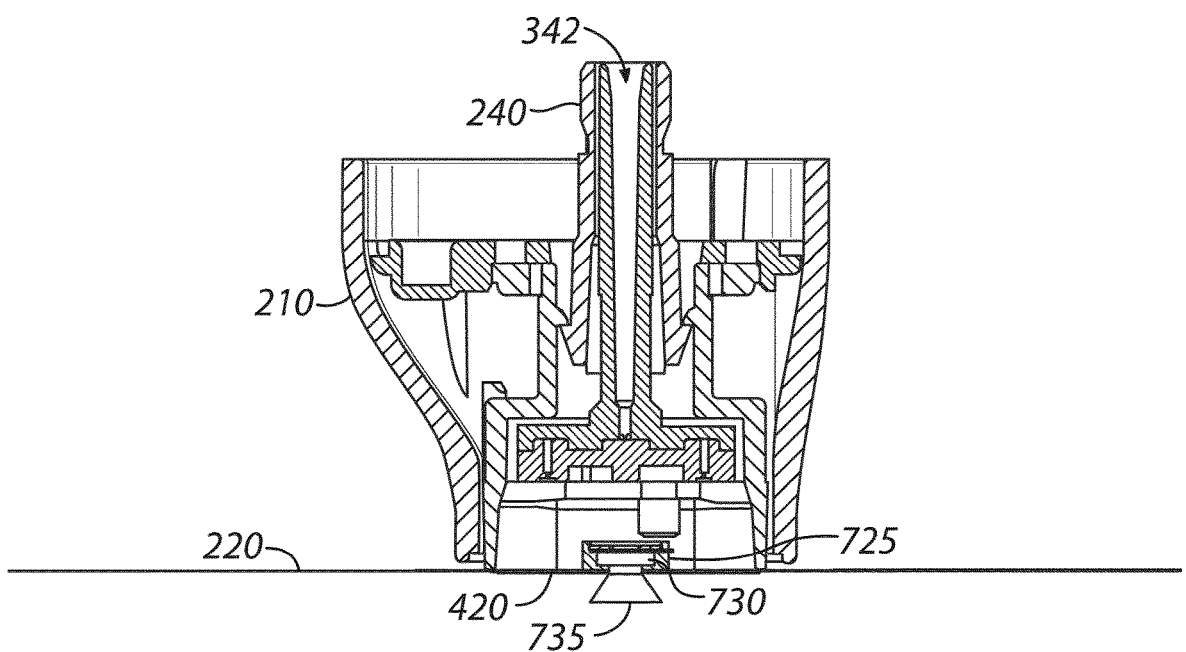
FIG. 3 is a lateral cross-sectional view of the example electrode assembly depicted in FIG. 2, in accordance with an embodiment of the invention described herein.

With reference to FIGS. 2 and 3, electrode assembly 150 includes a housing 210 that defines an outer periphery or shell of electrode assembly 150 and that is configured to detachably couple electrode assembly 150 with handpiece 140. Assembly housing 210 supports a flexible printed circuit 220, an extension flexible printed circuit 230 (FIG. 4), and a coolant conduit 240 defining a lumen 342 is coupled with a fluid path arranged within handpiece 140 to fluidly couple coolant source 160 with electrode assembly 150. The flexible printed circuits 220, 230 are depicted in an unfolded and unrouted state extending externally to the housing 210 for purposes of illustration, but would be arranged inside the interior of the housing 210 in a folded and routed state in an assembled electrode assembly 150.

Flexible printed circuit 220 may include a flexible substrate composed of a polymer, such as polyimide. The energy delivery circuit, which includes the electrode 420 and contact pads 410 (FIGS. 4-6), may include a patterned conductor, such as copper, that is formed on the flexible substrate. Similarly, extension flexible printed circuit 230 may also include a flexible substrate composed of a polymer, such as polyimide, and a patterned conductor providing a circuit (i.e., for the attached thermal sensor 730) that is formed on the flexible substrate.

Figure 4:
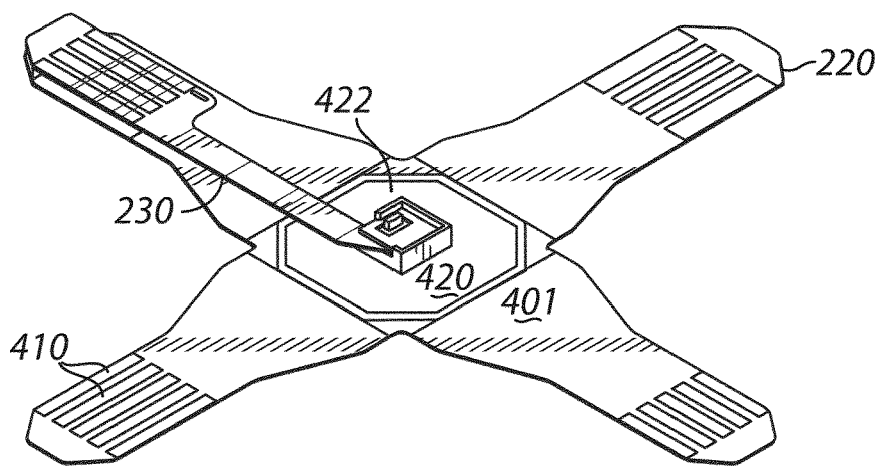
FIG. 4 is a perspective view of the flexible printed circuits of the example electrode assembly depicted in FIG. 2, in accordance with an embodiment of the invention described herein.
Figure 5:
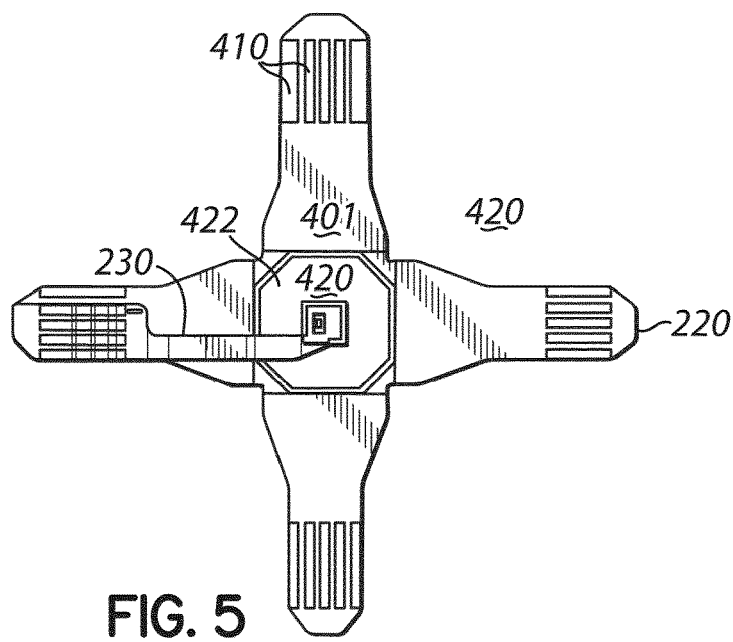
FIG. 5 is a top view of the flexible printed circuits depicted in FIG. 4.
Figure 6:
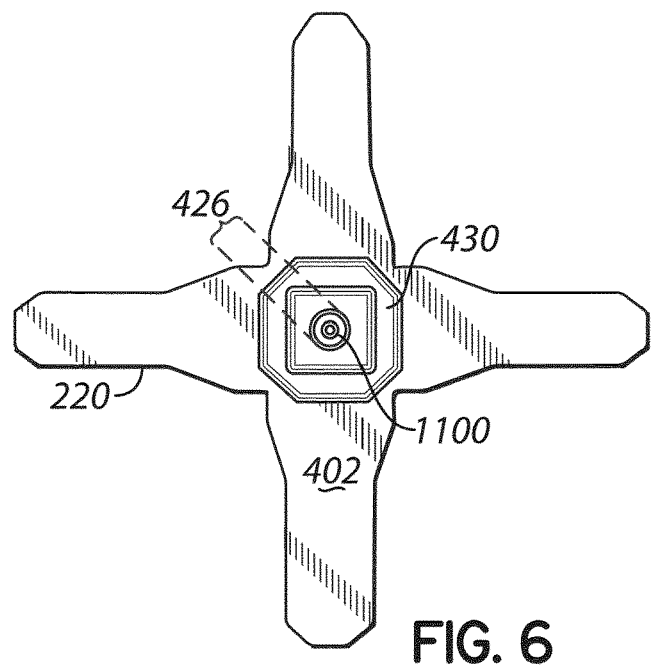
FIG. 6 is a bottom view of the flexible printed circuits depicted in FIG. 4.
Figure 7:
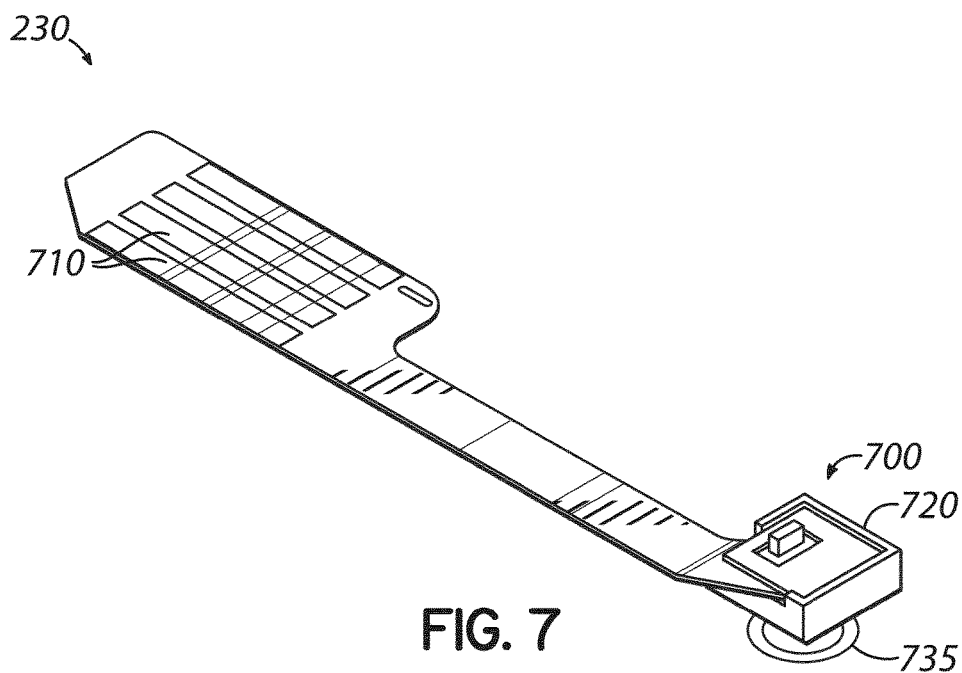
FIG. 7 is a perspective view of the extension flexible printed circuit depicted in FIG. 4.
Figure 8:
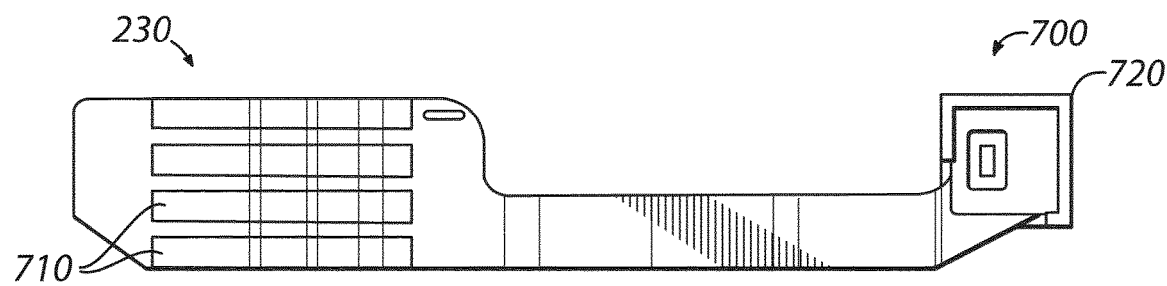
FIG. 8 is a top view of the extension flexible printed circuit depicted in FIG. 7.
Figure 9:
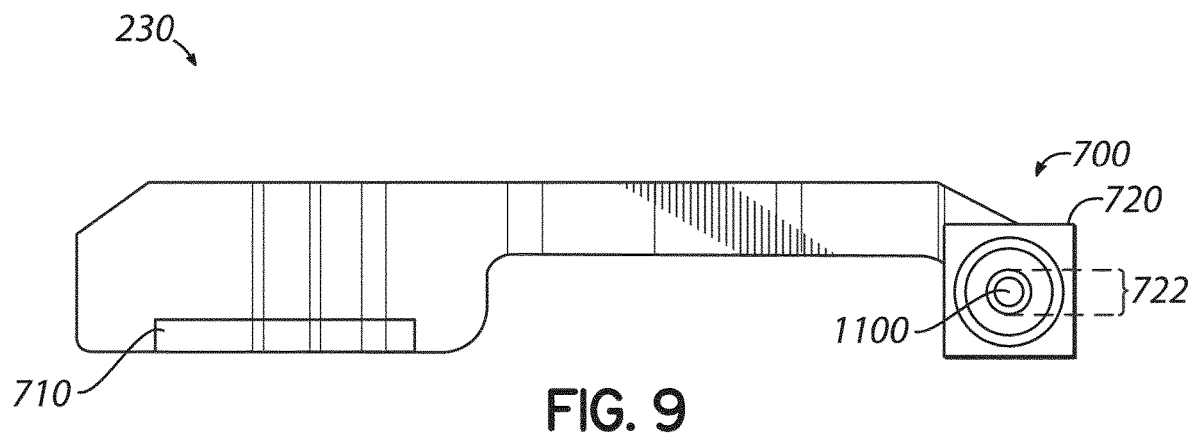
FIG. 9 is a bottom view of the extension flexible printed circuit depicted in FIG. 7.
Figure 10:
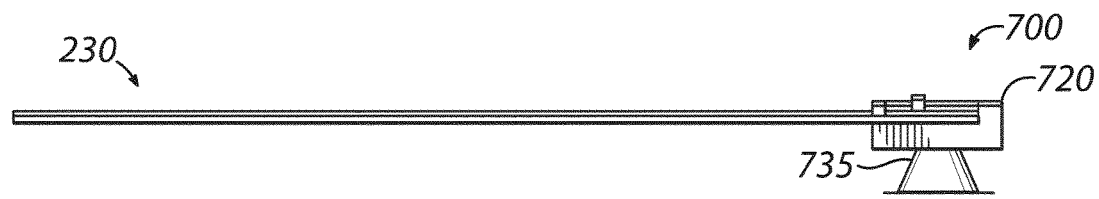
FIG. 10 is a side view of the extension flexible printed circuit depicted in FIG. 7.
Figure 11:
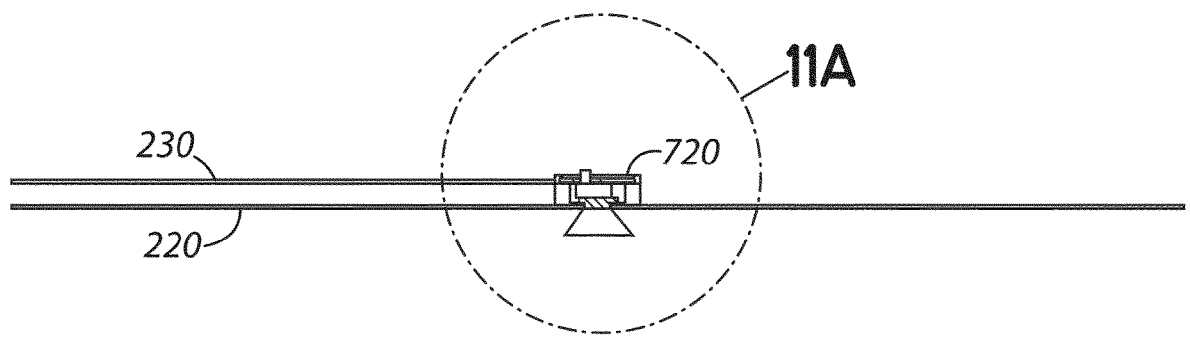
FIG. 11 is a side view of the flexible printed circuits depicted in FIG. 4.
Figure 11A:
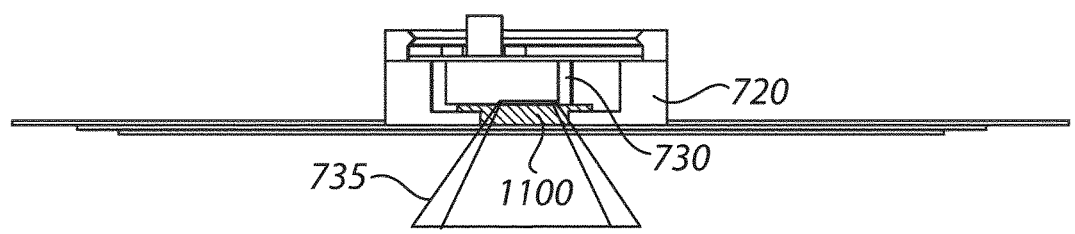
FIG. 11A is an enlarged side view of the circled portion of FIG. 11.
Figure 12:
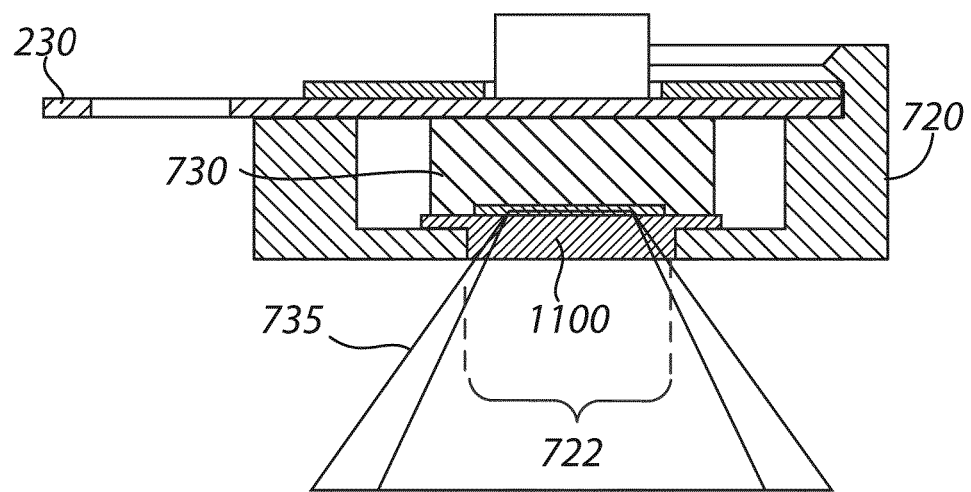
FIG. 12 is a cross-sectional detail view of the extension flexible printed circuit depicted in FIG. 11A.

With reference to FIGS. 4-6, the flexible printed circuit 220 comprises an energy delivery circuit that includes an electrode 420 configured to deliver electrical energy to a targeted area of a patient. The delivered electrical energy heats the tissue (e.g., skin tissue) beneath the targeted area. Electrode 420 receives the electrical energy from generator 130 via one or more contact pads 410 of the energy delivery circuit that participate in electrically coupling electrode 420 with generator 130. Generator 130 may utilize sensor data indicative of a temperature associated with the targeted area to regulate the electrical energy received by electrode 420.

In an embodiment, controller 110 may be further configured to regulate delivery of coolant by coolant source 160 to the non-patient facing side 401 of flexible printed circuit 220 and the interior surface 422 of electrode 420 based on sensor data generated by a thermal sensor 730. For example, sensor data generated by thermal sensor 730 and provided to the controller 110 may indicate that a temperature at the surface of the targeted area exceeds a defined threshold during the cosmetic procedure. Upon receiving such sensor data, controller 110 may cause coolant source 160 to increase the volume and/or frequency of coolant that is delivered to the interior surface 422, which lowers the temperature of the electrode 420 and increases the thermal gradient in the tissue beneath the targeted area.

In accordance with various embodiments, controller 110 may receive sensor data indicative of the temperature associated with the targeted area from a non-contact thermal sensing circuit 700 of extension flexible printed circuit 230 that includes the thermal sensor 730. Thermal sensor 730 may be included in a package that is surface mounted to extension flexible printed circuit 230. The package may include additional circuitry, such an analog-to-digital converter, one or more memories, a multiplexer, an amplifier, a digital circuit providing a state machine for local control, etc., that enables the operation of the thermal sensor 730. The sensing circuit 700 may include one or more contact pads 710 that participate in powering the sensing circuit 700 and communication data to and from the controller 110.

The thermal sensor 730 of the non-contact thermal sensing circuit 700 is configured to measure temperature at the surface of the targeted area during the cosmetic procedure. The thermal sensor 730 has a field of view 735 that extends beyond a patient-facing side 402 of flexible printed circuit 220 to the surface of the targeted tissue. The thermal sensor 730 is configured to measure the temperature without contacting the surface of the targeted tissue. In an embodiment, thermal sensor 730 may be implemented as an infrared temperature sensor that is configured to sense infrared radiation (i.e., black body radiation) emitted from the surface of the targeted tissue. The thermal sensor 730 may include a sensing element in the form of a thermopile having a set of connected thermocouples that are configured to convert thermal energy into electrical energy.

By measuring temperature at the surface of the targeted area during the cosmetic procedure, the thermal sensor 730 and non-contact thermal sensing circuit 700 output sensor data with improved accuracy relative to sensor data output by thermistors conventionally attached to non-patient facing side 401 of flexible printed circuit 220. For example, the thermal sensor 730 is not affected by artifacts (e.g., pooling or flooding) from cryogen sprayed on the non-patient facing side 401 of flexible printed circuit 220 as are thermistors.

Thermal sensor 730 may avoid or mitigate the various challenges associated with using thermistors. Intervening elements between any thermistors positioned on the non-patient facing side 401 of flexible printed circuit 220 and the targeted area proximate to an exterior surface of electrode 420 may include flexible printed circuit 220 and any other elements formed on flexible printed circuit 220, such as polyimide films or a dielectric standoff material 430. Implementing non-contact thermal sensing circuit 700 avoids or substantially reduces the effect of such intervening elements, as discussed in greater detail below. For example, non-contact thermal sensing circuit 700 measures the temperature at the surface of the targeted area without the need for inferences or extrapolation from thermistor data.

With reference to FIGS. 7-10, a sensor housing 720 is provided in some embodiments to position thermal sensor 730 within assembly housing 210 relative to an aperture (e.g., aperture 426 of FIG. 6) of electrode 420. The aperture 426 may fully penetrate through the thickness of the flexible printed circuit 220 at the location of electrode 420 to provide an unobstructed path or substantially unobstructed path permitting temperature measurements by the thermal sensor 730. The aperture 426 may extend through the conductor of electrode 420 and the flexible substrate of flexible printed circuit 220. In an embodiment, the aperture 426 may only extend through the electrode 420 such that the substrate of the flexible printed circuit 220 remains inside the aperture 426 and the aperture 426 is a blind opening in which a portion of the substrate is located between the thermal sensor 730 and the surface of the targeted area when electrode 420 is positioned proximate to the targeted area during the cosmetic procedure. Sensor housing 720 also includes an aperture 722 that facilitates the field of view 735 extending beyond the patient-facing side 402 of flexible printed circuit 220. To that end, aperture 722 may be configured to be substantially aligned with aperture 426. In an embodiment, the aperture 426 may be circular and may have a diameter in a range of about 0.5 millimeters (mm) to about 5.0 mm, or about 1.0 mm to about 3.0 mm, or about 1.0 mm to about 2.5 mm, or about 1.5 mm to about 2.0 mm.

In various embodiments, a window 1100 may be positioned between thermal sensor 730 and the surface of the targeted area when electrode 420 is positioned proximate to the targeted area during the cosmetic procedure. The window 1100 may reduce a likelihood that foreign substances (e.g., coupling gel or liquid utilized with some cosmetic procedures) enter sensor housing 720 via apertures 426, 722 and interfere with operation of thermal sensor 730. In an embodiment, window 1100 may comprise a long-pass optical filter configured to pass optical energy having wavelengths within an infrared region of the electromagnetic spectrum. In an embodiment, window 1100 may be composed of silicon, zinc selenide, germanium, zinc sulfide, calcium fluoride, or a combination thereof. In an embodiment, window 1100 may be mounted within the aperture 426 and may be supported by the material of the flexible printed circuit 220 surrounding aperture 722. In an embodiment, the window 1100 may be integrated into the thermal sensor 730 and is not a separate element. In an embodiment, the window 1100 may be positioned inside or on the housing 210 between the thermal sensor 730 and the surface of the targeted area during the cosmetic procedure.

During a cosmetic procedure, thermal sensor 730 generates sensor data indicative of temperature at the surface of the targeted area of the patient by converting the received infrared radiation into an electrical signal. The sensor data generated by thermal sensor 730 may be communicated to a feedback circuit of controller 110. In an embodiment, controller 110 is configured to regulate electrical energy provided to electrode 420 based on sensor data generated by thermal sensor 730. For example, based on such sensor data, controller 110 may cause generator 130 modify an amplitude or a duty cycle of electrical energy provided to electrode 420.

Sensor housing 720 may include materials that mitigate any impact of environmental factors on the accuracy of sensor data generated by thermal sensor 730 during a cosmetic procedure and thereby provide operational stability. For example, electromagnetic radiation associated with delivery of electrical energy to the targeted area may impart electromagnetic interference on sensor data that thermal sensor 730 generates during a cosmetic procedure. In an embodiment, sensor housing 720 comprises a material 725 configured to absorb electromagnetic radiation associated with delivery of electrical energy to a targeted area and thereby shield the thermal sensor. The shielding material 725 may comprise, for example, a silver-filled electrically-conductive epoxy that resides in the portion of the space inside the assembly housing 210 proximate to the sensor housing 720 and may be applied as a coating of material on the sensor housing 720. The material 725 may be effective to alleviate any impact of electromagnetic interference on the accuracy of sensor data generated by thermal sensor 730 during a cosmetic procedure.

In an alternative embodiment, the material 725 may be a thermally-resistive material that is configured to thermally isolate temperature sensor 730 from coolant applied to the interior surface 422 of electrode 420. The thermally-resistive material may be a polymer such as polytetrafluoroethylene (PTFE), a polycarbonate (PC) and polyethylene terephthalate (PC/PET) blend, or a polycarbonate/acrylonitrile butadiene styrene (PC/ABS) blend, a ceramic such as aluminum oxide, zirconium oxide, or a silicate, or a rigid foam such as a polyurethane rigid (PUR) foam or a polyisocyanurate rigid (PIR) form. In this embodiment, the material 725 may alleviate any impact of the coolant delivered during a cosmetic procedure on the accuracy of sensor data generated by thermal sensor 730 during a cosmetic procedure may be avoided or mitigated.

Figure 13:
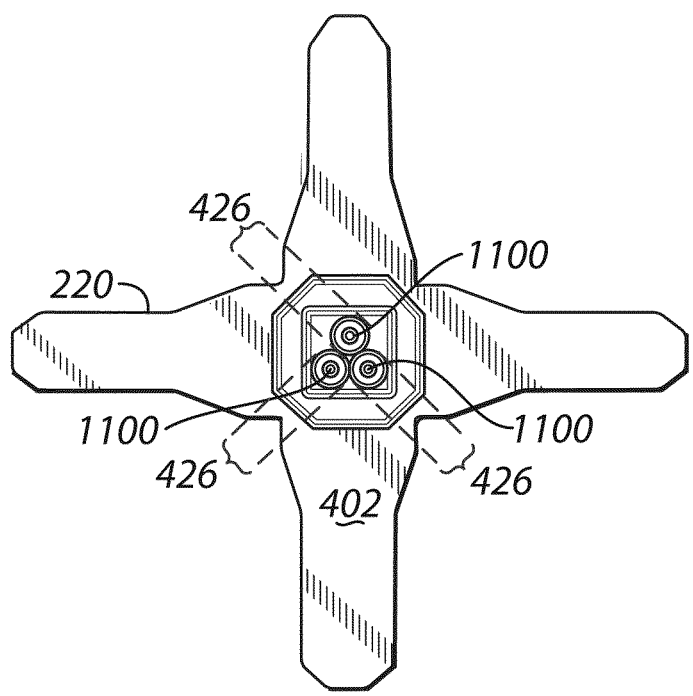
FIG. 13 is a bottom view of flexible printed circuits of the example electrode assembly depicted in FIG. 2 that include multiple thermal sensors in accordance with an embodiment of the invention described herein.

With reference to FIG. 13 and in an embodiment, thermal sensor 730 may be one of multiple thermal sensors arranged inside assembly housing 210. In an embodiment, data indicative of a temperature distribution across multiple positions of a surface of a targeted area may be acquired using the multiple thermal sensors. In an embodiment in which thermal sensor 730 is one of multiple thermal sensors, each thermal sensor among the plurality of thermal sensors may be positioned within a different aperture 426 of electrode 420.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed:

1. An electrode assembly comprising:
   a first housing;
   an electrode inside the first housing, the electrode configured to deliver electrical energy to a targeted area of a patient, and the electrode including a first aperture;
   a first flexible circuit that includes the electrode;
   a second flexible circuit; and
   a first thermal sensor inside the first housing, the first thermal sensor mounted to the second flexible circuit, the first thermal sensor positioned relative to the first aperture of the electrode to provide a first field of view through the first aperture to a surface of the targeted area, and the first thermal sensor configured to generate first sensor data indicative of a temperature at the surface of the targeted area.

2. The electrode assembly of claim 1 wherein the first thermal sensor is an infrared temperature sensor.

3. The electrode assembly of claim 1 further comprising:
   a window positioned on the first housing between the first thermal sensor and the surface of the targeted area.

4. The electrode assembly of claim 3 wherein the window is a long-pass optical filter configured to pass optical energy having wavelengths within an infrared region of the electromagnetic spectrum.

5. The electrode assembly of claim 3 wherein the window is located within the first aperture.

6. The electrode assembly of claim 3 wherein the window comprises silicon, zinc selenide, germanium, zinc sulfide, calcium fluoride, or a combination thereof.

7. The electrode assembly of claim 1 wherein the electrode includes a second aperture, and further comprising:
   a second thermal sensor inside the first housing, the second thermal sensor positioned relative to the second aperture in the electrode to provide a second field of view through the second aperture to the surface of the targeted area, and the second thermal sensor configured to generate second sensor data indicative of the temperature at the surface of the targeted area.

8. The electrode assembly of claim 1 further comprising:
a second housing configured to support the first thermal sensor and to position the first thermal sensor within the first housing relative to the first aperture.

9. The electrode assembly of claim 8 wherein the second housing comprises a thermally-resistive material configured to thermally isolate the first thermal sensor from a space between the first housing and the second housing.

10. The electrode assembly of claim 8 wherein the second housing comprises a shielding material configured to absorb electromagnetic radiation associated with the electrical energy delivered from the electrode to the targeted area.

11. The electrode assembly of claim 1 wherein the first flexible circuit includes a flexible substrate, and the first aperture further extends through the flexible substrate.

12. The electrode assembly of claim 11 further comprising:
a window positioned inside the first housing between the first thermal sensor and the surface of the targeted area.

13. The electrode assembly of claim 12 wherein the window comprises silicon, zinc selenide, germanium, zinc sulfide, calcium fluoride, or a combination thereof.

14. The electrode assembly of claim 12 wherein the window is a long-pass optical filter configured to pass optical energy having wavelengths within an infrared region of the electromagnetic spectrum.

15. The electrode assembly of claim 12 wherein the window is located within the first aperture.

16. The electrode assembly of claim 1 further comprising:
a window positioned inside the first housing between the first thermal sensor and the surface of the targeted area.

17. An apparatus comprising:
an electrode assembly including a housing, an electrode inside the housing, a first flexible circuit that includes the electrode, a second flexible circuit, and a thermal sensor inside the housing, the electrode configured to deliver electrical energy to a targeted area of a patient, the thermal sensor mounted to the second flexible circuit, the electrode including an aperture, and the thermal sensor positioned relative to the aperture to provide a field of view through the aperture of the electrode to a surface of the targeted area, and the thermal sensor configured to generate sensor data indicative of a temperature at the surface of the targeted area;
a handpiece configured to removably receive the electrode assembly;
a generator coupled to the electrode assembly, the generator configured to generate the electrical energy; and
a controller coupled to the generator, the electrode, and the thermal sensor, the controller configured to regulate the electrical energy generated by the generator based on the sensor data.

18. A method comprising:
attaching a non-contact thermal sensor to a first flexible printed circuit;
forming an aperture extending through an electrode of a second flexible printed circuit; and
assembling the first flexible printed circuit and the second flexible printed circuit inside of a housing,
wherein the non-contact thermal sensor is positioned inside the housing with a field of view through the aperture in the electrode.

19. The method of claim 18 further comprising:
positioning a window inside the aperture.

20. The method of claim 18 further comprising:
surrounding the non-contact thermal sensor with a first material configured to provide thermal isolation or a second material configured to absorb electromagnetic radiation.

* * * * *